United States Patent
Uber, III et al.

(10) Patent No.: US 7,672,710 B2
(45) Date of Patent: Mar. 2, 2010

(54) DATA COMMUNICATION AND CONTROL FOR MEDICAL IMAGING SYSTEMS

(75) Inventors: Arthur E. Uber, III, Pittsburgh, PA (US); Edward J. Rhinehart, Monroeville, PA (US); Rosemary Almon-Martin, Saxonburg, PA (US); David M. Griffiths, Pittsburgh, PA (US); Alan D. Hirschman, Glenshaw, PA (US); Francis J. Sciulli, Crafton, PA (US); Walter Grumski, Pittsburgh, PA (US); Karen Zelenski, Cranberry Township, PA (US)

(73) Assignee: Medrad, Inc., Indianola, PA (US)

( * ) Notice: Subject to any disclaimer, the term of this patent is extended or adjusted under 35 U.S.C. 154(b) by 1042 days.

(21) Appl. No.: 11/196,806

(22) Filed: Aug. 2, 2005

(65) Prior Publication Data

US 2006/0030773 A1    Feb. 9, 2006

Related U.S. Application Data

(60) Continuation of application No. 10/134,858, filed on Apr. 29, 2002, now Pat. No. 6,970,735, which is a division of application No. 09/300,326, filed on Apr. 27, 1999, now Pat. No. 6,397,098, which is a continuation-in-part of application No. 09/197,773, filed on Nov. 23, 1998, now Pat. No. 6,385,483, which is a division of application No. 08/309,820, filed on Sep. 21, 1994, now Pat. No. 5,840,026.

(51) Int. Cl.
*A61B 6/00* (2006.01)
*A61M 5/30* (2006.01)
*A61M 5/00* (2006.01)

(52) U.S. Cl. .................. 600/431; 604/65; 604/246

(58) Field of Classification Search ................ 600/431, 600/407, 411, 432, 433, 434, 435, 65, 66, 600/67, 246; 604/65, 66, 67, 246
See application file for complete search history.

(56) References Cited

U.S. PATENT DOCUMENTS 3,520,295 A     7/1970    Kelly (Continued)

FOREIGN PATENT DOCUMENTS

EP          0121216         10/1984

(Continued)

OTHER PUBLICATIONS

*Tyco Healthcare Group LP v. MEDRAD, Inc.* Complaint, Case No. 1:06-cv-00763, Nov. 8, 2006.

(Continued)

*Primary Examiner*—Daniel L Robinson
(74) *Attorney, Agent, or Firm*—Gregory L. Bradley; James R. Stevenson

(57) ABSTRACT

A system for producing a contrast-enhanced medical image of a patient includes a source of a contrast or enhancement medium, a pressurizing unit in fluid connection with the source of contrast or enhancement medium, an energy source operable to apply energy to a region of the patient, an imaging unit providing a visual display of an internal view of the patient based upon a signal resulting from the energy applied to the region of the patient, and a control unit. In an embodiment, the signal is affected by a condition of the contrast or enhancement medium in the patient. To control the procedures, the control unit adjusts the condition of the contrast or enhancement medium in the patient based upon the signal. A communication interface preferably enables information between an injector subsystem and an imaging subsystem.

43 Claims, 6 Drawing Sheets

U.S. PATENT DOCUMENTS

| | | | |
|---|---|---|---|
| 3,523,523 A | 8/1970 | Heinrich et al. | |
| 4,151,845 A | 5/1979 | Clemens | |
| 4,263,916 A | 4/1981 | Brooks et al. | |
| 4,280,494 A | 7/1981 | Cosgrove, Jr. et al. | |
| 4,392,847 A | 7/1983 | Whitney et al. | |
| 4,392,849 A | 7/1983 | Petre et al. | |
| 4,448,200 A | 5/1984 | Brooks et al. | |
| 4,477,923 A * | 10/1984 | Baumann et al. | 378/95 |
| 4,504,908 A | 3/1985 | Riederer et al. | |
| 4,542,459 A | 9/1985 | Riederer | |
| 4,578,802 A | 3/1986 | Itoh | |
| 4,611,340 A | 9/1986 | Okazaki | |
| 4,612,572 A | 9/1986 | Komatsu et al. | |
| 4,672,651 A | 6/1987 | Horiba et al. | |
| 4,676,776 A | 6/1987 | Howson | |
| 4,689,670 A | 8/1987 | Okazaki | |
| 4,723,261 A | 2/1988 | Janssen et al. | |
| 4,854,324 A * | 8/1989 | Hirschman et al. | 600/432 |
| 4,903,705 A | 2/1990 | Imamura et al. | |
| 4,913,154 A * | 4/1990 | Ermert et al. | 600/431 |
| 4,922,916 A * | 5/1990 | Ermert et al. | 600/425 |
| 4,943,987 A | 7/1990 | Asahina et al. | |
| 4,947,412 A | 8/1990 | Mattson | |
| 4,965,726 A | 10/1990 | Heuscher et al. | |
| 4,995,064 A | 2/1991 | Wilson et al. | |
| 5,010,473 A | 4/1991 | Jacobs | |
| 5,018,173 A | 5/1991 | Komai et al. | |
| 5,034,987 A | 7/1991 | Fujimoto et al. | |
| 5,054,044 A | 10/1991 | Audon et al. | |
| 5,111,492 A | 5/1992 | Klausz | |
| 5,123,056 A | 6/1992 | Wilson | |
| 5,125,018 A | 6/1992 | Asahina | |
| 5,150,292 A | 9/1992 | Hoffmann et al. | |
| 5,166,961 A | 11/1992 | Brunnett et al. | |
| 5,190,744 A | 3/1993 | Rocklage et al. | |
| 5,215,095 A | 6/1993 | Macvicar et al. | |
| 5,228,070 A | 7/1993 | Mattson | |
| 5,249,122 A | 9/1993 | Stritzke | |
| 5,249,579 A | 10/1993 | Hobbs et al. | |
| 5,262,946 A | 11/1993 | Heuscher | |
| 5,276,614 A | 1/1994 | Heuscher | |
| 5,286,252 A | 2/1994 | Tuttle et al. | |
| 5,287,273 A | 2/1994 | Kupfer et al. | |
| 5,301,672 A * | 4/1994 | Kalender | 600/428 |
| 5,417,213 A * | 5/1995 | Prince | 600/413 |
| 5,544,215 A * | 8/1996 | Shroy et al. | 378/98.12 |
| 5,799,649 A * | 9/1998 | Prince | 600/420 |

FOREIGN PATENT DOCUMENTS

| | | |
|---|---|---|
| EP | 0129910 | 1/1985 |
| EP | 0121216 | 8/1988 |
| EP | 0192786 | 2/1990 |
| EP | 0364966 | 4/1990 |
| EP | 0245160 | 5/1990 |
| EP | 0372152 | 6/1990 |
| EP | 0378896 | 7/1990 |
| EP | 0429191 | 5/1991 |
| EP | 0471455 | 2/1992 |
| EP | 0475563 | 3/1992 |
| EP | 0595474 | 5/1994 |
| EP | 0365301 | 8/1994 |
| EP | 0619122 | 10/1994 |
| GB | 201800 | 10/1979 |
| JP | 60-194934 | 10/1985 |
| JP | 60-194935 | 10/1985 |
| JP | 60-253197 | 12/1985 |
| JP | 62-216199 | 9/1987 |
| JP | 63-040538 | 2/1988 |
| JP | 01-207038 | 8/1989 |
| JP | 02-234747 | 9/1990 |
| JP | 03-055040 | 3/1991 |
| JP | 04-115677 | 4/1992 |
| WO | WO9114232 | 9/1991 |
| WO | WO9114233 | 9/1991 |
| WO | WO9315658 | 8/1993 |
| WO | WO9325141 | 12/1993 |

OTHER PUBLICATIONS

ANGIOMAT 6000 Digital Injection System Operator's Manual 600950 Rev. 1, Liebel-Flarsheim Company, 1990.

MCT and MCT Plus Injection Systems Operation Manual KMP 810P, MEDRAD, Inc, 1991.

Mark V/Mark V Plus Injector Operation Manual KMP 805P Rev. B, MEDRAD, Inc, 1990.

* cited by examiner

SEQUENCE NUMBERS BEFORE MESSAGE TRANSMISSION.

SEQUENCE NUMBERS AFTER THE INJECTOR HAS SENT A MESSAGE AND THE EXTERNAL DEVICE RECIEVED AND VALIDATED IT.

SEQUENCE NUMBERS AFTER EXTERNAL DEVICE ACKNOWLEDGED THE RECIEVED MESSAGE AND THE INJECTOR RECEIVED THE ACKNOWLEDGE.

DATA COMMUNICATION AND CONTROL FOR MEDICAL IMAGING SYSTEMS

CROSS-REFERENCE TO RELATED APPLICATIONS

The present application is a continuation of U.S. patent application Ser. No. 10/134,858, filed Apr. 29, 2002 now U.S. Pat. No. 6,970,735, which is a divisional of U.S. patent application Ser. No. 09/300,326, filed on Apr. 27, 1999 now U.S. Pat. No. 6,397,098, which is a continuation-in-part of U.S. patent application Ser. No. 09/197,773, filed on Nov. 23, 1998 now U.S. Pat. No. 6,385,483, which is a divisional of U.S. patent application Ser. No. 08/309,820, filed on Sep. 21, 1994, now U.S. Pat. No. 5,840,026, the disclosures of which are incorporated herein by reference.

BACKGROUND OF THE INVENTION

The present invention relates generally to data communication and control, and, more particularly, to devices, systems and methods for communication of data and control based thereon in contrast-enhanced medical imaging systems.

It is well recognized that the appropriate dose for many medications is related to a number of variables, including, for example, the size, weight, or physiologic state of the patient being treated. This variation is readily apparent from the different recommended doses many medications have for adults and children. The appropriate dose of contrast media for a given medical imaging procedure is equally dependent upon the size and weight of the patient being examined as well as additional factors.

Although differences in dosing requirements for medical imaging procedures have been recognized, many conventional medical imaging procedures, including angiographic, computed tomography, magnetic resonance and ultrasound imaging, continue to use pre-set doses or standard delivery protocols for injecting contrast media during medical imaging procedures. Although using fixed protocols for delivery simplifies the procedure, providing the same amount of contrast media to patients of widely varying size and weight can produce very different results in image contrast and quality.

Some of the shortcomings of existing procedures have been addressed and resolved as described in U.S. Pat. No. 5,806,519, issued Sep. 15, 1998, the disclosure of which is incorporated herein by reference. U.S. Pat. No. 5,806,519 discloses a contrast media delivery system that provides a source of contrast media sufficiently isolated from a patient undergoing an imaging procedure that the source of contrast media may be used on additional patients without concern for contamination. Additionally, the system is capable of adjusting contrast media concentration and other injection parameters during an injection procedure. The term "concentration" refers generally to the concentration of the image enhancing agents, particles or chemicals, in the contrast media.

The system of U.S. Pat. No. 5,806,519 incorporates a source of contrast media and, if desired, an admixture to dilute the media. If there is an admixture, then the contrast media preferably has a concentration which is the highest that would be used in an injection procedure so that the operator may combine the contrast media with the admixture and select virtually any concentration of contrast media desired for any given procedure. The concentration of the contrast media injected into a patient may be varied during the injection procedure by varying the ratio of admixture to contrast media. Each patient thus receives only the amount of contrast media necessary to provide a proper diagnostic image.

It has been recognized that the system of U.S. Pat. No. 5,806,519 is much more versatile and useful if the operator is able to select and adjust contrast media concentration and other injection parameters based on patient information and/or feedback received during the injection imaging procedures. U.S. patent application Ser. No. 09/197,773 and U.S. Pat. No. 5,840,026 disclose such systems. Those systems are capable of automatically choosing the appropriate concentration and injection rate for a given patient and are capable of automatically adjusting concentration and other injection parameters during an injection procedure based on feedback related to the resultant image quality.

Although significant strides have thus been achieved in the control of contrast-enhanced, medical imaging procedures, it remains desirable to develop improved devices, systems and methods for communication of data between devices and control based thereon in contrast-enhanced medical imaging systems.

SUMMARY OF THE INVENTION

The present invention provides several systems, devices and methods for producing a contrast-enhanced medical image of a patient. According to one embodiment, such a system includes generally a source of a contrast or enhancement medium and a pressurizing unit in connection with the source of contrast or enhancement medium to pressurize the contrast or enhancement medium for injection into the patient. The contrast medium or enhancement medium is also called the fluid medium, being a liquid, gas, or solid suspended in a liquid or a gas. The system also includes an energy source adapted to apply energy to a region of the patient and an imaging unit providing (preferably in real-time) an indication (for example, a visual or audible indication) of an internal state, condition or view of the patient based upon a signal resulting from the energy applied to the region of the patient. This signal is affected by a condition of the contrast or enhancement medium in the patient. The system also includes a control unit adapted to adjust the condition of the contrast or enhancement medium in the patient based upon the signal resulting from the energy applied to the region of the patient. The system may include general components or pieces of equipment manufactured by more than one company, for instance, an injector and an imager.

The condition of the fluid medium flowing into the patient can, for example, correspond to at least one parameter including, but not limited to, contrast medium concentration, flow rate of the contrast medium, timing of an injection, sequencing of more than one injection (of the same or different contrast media), injected volume of the contrast medium, injection pressure of the contrast medium or temperature of the contrast medium.

Although U.S. Pat. No. 5,840,026 describes generally the use of the pixel intensity of one or more portions or regions of the visual display of an imaging unit to control one or more conditions of the fluid medium within the patient, the present inventors have also discovered that direct use or modification of the raw signal used to produce the image may have certain significant advantages in controlling the imaging procedure. For example, a portion of the information available from the raw signal may be lost or distorted in various compression algorithms that are used to address the limited dynamic range of the displays that are available to show an image. The energy applied to the region of the patient may, for example, be sonic energy, in which case the raw signal is an acoustic intensity signal. This particular method is sometimes called acoustic intensitometry or acoustic densitometry. The energy may, for example, also be penetrating radiation such as X-rays, or non-ionizing electromagnetic radiation such as light.

The present invention also provides another embodiment of a system for producing a contrast-enhanced medical image of a patient including a source of a fluid medium and a pressurizing unit as described above. As used herein, the terms "image" or "view" refer generally to an indication of an internal condition or state of a patient and are not limited to a visual display. The system also includes an energy source and an imaging unit to provide (preferably in real-time) an indication (for example, a visual display) of an internal view of the patient based upon a signal resulting from the energy applied to the region of the patient. In this embodiment, the system further includes a control unit adapted to adjust the condition (as described above) of the fluid medium in the patient to maintain at least one portion of the indication (for example, a portion of a visual display) at a desired level of intensity or enhancement. For example, the control unit can adjust the condition of the fluid medium flowing into the patient based upon the signal resulting from the imaging energy applied to the region of the patient. The system can also adjust the condition of the fluid medium flowing into the patient based upon measured intensity or density of the portion of a visual display. Such control of the imaging procedure assists in the study of, for example, lesions in the region of interest.

In another embodiment, the control unit adjusts parameters of the imaging unit to obtain an optimum or sufficient image based upon the concentration of the contrast-enhancing agent flowing into the patient. Possible adjusted parameters include but are not limited to: the power in the signal sent into the patient, the time during which the energy is applied to the patient, the gain of the amplifier which receives the signal from the patient, or the speed at which the energy is scanned across the patient.

The present invention also provides a system for delivering an active substance (for example, a biologically active therapeutic substance or a diagnostic substance) to a patient including a source of a fluid medium that incorporates the active substance and a contrast agent. A pressurizing unit is in fluid connection with the source of fluid medium to pressurize the fluid medium for injection into the patient. The system also includes an imaging energy source adapted to apply imaging energy to a region of the patient and an imaging unit providing a visual display (preferably in real-time) of an internal view of the patient based upon a signal resulting from the imaging energy applied to the region of the patient. The system further includes a control unit adapted to control delivery of the active substance by adjusting the condition of the contrast agent in the patient.

In this embodiment, the active substance is preferably activated by activation energy from a source of activation energy. The activation energy and the imaging energy can be the same or different types of energy. In general, the concentration of the active substance in a region of interest will be directly proportional to the concentration or amount of contrast agent in the region of interest. The strength and duration of the applied activation energy can, for example, be adjusted based upon the signal resulting from the imaging energy or upon the resulting visual or other (for instance sound pitch, sound volume, numeric readout, or meter readout) indication provided to the user (preferably in real-time). The contrast medium and the active substance may be combined. For example, a therapeutic drug or a gene therapy may be contained in partially gas filled microspheres that are ruptured by ultrasound energy beamed into a specific part of the body to activate the therapeutic drug or gene therapy.

The present invention further provides another system for producing a contrast-enhanced medical image of a patient similar to the systems described above. In this embodiment, however, the control unit is adapted to time injection of at least one discrete flow interval of fluid medium based, for example, upon at least one of a visual display or a signal resulting from application of the imaging energy to a region of the patient (both may be used simultaneously). In one embodiment, the discrete flow interval may be a bolus of fluid medium.

Preferably, unidirectional or bi-directional communication and optionally control between devices of the present invention is enabled through use of a control/communication interface to which each of the devices of the imaging/injection system can be connected. This interface mating point can be located on a separate device or can be incorporated into one of the other devices (for example, into a controller for the pressurizing unit or injector). Suitable communication methods include data transmission, preferably digital, over wires, fiber optics, or via conducted or broadcast electromagnetic radiation (for example, light and RF) or ultrasonic radiation.

The communication interface of the present invention is a substantial improvement over previous systems that merely communicated timing information via relay closures. In the present invention, data transmission includes information sent between devices regarding operating parameters, operator input, device status information, and/or control sequencing. In addition, data transferred from one device to another device in the present invention can be used to enable active control of the receiving device from that data. For example, during the injecting state, data transmission from an ultrasound imager can be sent to an injector to enable active control of the injection flow rate based on the data received. Currently available systems merely relay analog closures between an injector and an imager to communicate the timing of certain states and are not used for data transmission or communication. In such systems, the relay closure causes the injector or imager subsystem to begin executing a preset program. In the present invention on the other hand, data on the status of one subsystem is communicated to the other subsystem for use by that subsystem. The receiving subsystem may alter its operation based upon this information, even to the extent of being programmed by the transmitting subsystem. Moreover, digital communication enabled by the present invention allows much more information to be conveyed than a simple relay closure.

Preferably the communicating devices use the same protocol so that the information being communicated does not need to be converted. Note that it is also possible for the devices to support multiple communication protocols, which may be selected by the user or selected by automatic negotiation between the communicating devices.

In addition, the present invention provides methods for adjusting the condition of a fluid medium (as described above) during an imaging procedure. In one embodiment, the method includes pressurizing the fluid medium for injection into the patient. Further, the method includes supplying energy to a region of the patient and indicating (preferably in real-time) an internal view (that is, a condition or state) of the patient based upon a signal resulting from the energy applied to the region of the patient. This signal is affected by a condition of the fluid medium in the patient as described above. The method further comprises the step of adjusting the condition of the fluid medium in the patient based upon the signal resulting from the energy applied to the region of the patient.

In another method, the condition of the fluid in the patient is adjusted to maintain at least one portion of the indication (for example, a portion of a visual display) at a desired level of intensity/density or intensity/density profile over time. For example, the control unit can adjust the condition of the fluid medium in the patient based upon the signal resulting from the energy applied to the region of the patient to provide enhancement in the region of interest that is constant or varies within some acceptable range. The system can also adjust the condition of the fluid in the patient based upon measured intensity of the portion of a visual display or measured intensity of an acoustic indicator. As discussed above, such control of the imaging procedure can assist, for example, in the study of lesions in the region of interest.

The present invention also provides a method for delivering an active substance to a patient, comprising the step of controlling delivery or administration of the active substance by adjusting the condition of the contrast agent in the patient. As described above, the active substance is preferably activated by activation energy from a source of activation energy. The activation energy and the imaging energy can be the same or different types of energy.

The present invention also provides for structured communications in the situation where the control unit functions are shared between two or more pieces of equipment.

For example, the present invention provides a system for control of an imaging procedure comprising: a source of a contrast or enhancement medium; a pressurizing unit in fluid connection with the source of contrast or enhancement medium to pressurize the contrast or enhancement medium for injection of the contrast or enhancement medium into the patient; an imaging energy source adapted to apply imaging energy to a region of the patient; an imaging unit providing an indication (for example, a visual display) of an internal view of the patient based upon a signal resulting from the imaging energy applied to the region of the patient, the signal being affected by a condition of the contrast or enhancement medium in the patient; and a data communication interface between at least the pressurizing unit and the imaging unit to enable exchange of data between the pressurizing unit and the imaging unit. Preferably, the exchange of data is bi-directional. Moreover, the data is preferably in digital form.

The present invention also provides an injector system for producing a contrast-enhanced medical image of a patient in cooperation with an imaging system. As described above, the imaging system applies energy to a patient and produces an image or a measurement of a region of interest in the patient from a signal resulting from the applied energy. The injector system preferably comprises: a source of a contrast or enhancement medium; a pressurizing subsystem in connection with the source of contrast or enhancement medium to pressurize the contrast or enhancement medium for injection into the patient; an injector control unit for controlling said pressurizing subsystem; and a communication interface to exchange data between the injector system and the imaging system.

The injector system may communicate information from the injector system to the imaging system. Likewise, the imaging system may communicate data or information from the imaging system to the injector system. Such communication can be unidirectional or bi-directional. The injector control unit may modify one or more parameters of the injection based upon the data or information from the imaging system. The imaging control unit may also modify one or more parameters of the imager unit based on the data or information sent from the injector. The injector system may further contain an electrically and/or physically isolated (wireless) interface through which the communication interface exchanges data or information with the imaging unit.

The present invention also provides an imaging unit for producing a contrast-enhanced medical image of a patient in cooperation with an injector system. As described above, the injector system pressurizes a contrast or enhancement medium for injection into the patient. The imaging unit preferably comprises: a source of energy to be applied to a region of interest in the patient; a display to provide an image based upon a signal resulting from the imaging energy applied to the region of the patient; an imaging control unit for controlling the imaging unit; and a communication interface to exchange data or information between the injector system and the imaging unit.

Communication of data/control may be from the injector system to the imaging unit or visa versa and either uni- or bi-directional. The imaging unit preferably further contains an electrically and/or physically isolated interface through which the communication interface shares information with the injector system.

The interface is preferably in communicative connection with at least the pressurizing unit and the imaging unit to enable sharing and exchanging of data between the pressurizing unit and the imaging unit.

The above and other systems, devices and methods of the present invention, and their attendant advantages, will become even more apparent to one skilled in the art upon consideration of the following detailed description in combination with the accompanying drawings.

DETAILED DESCRIPTION OF THE INVENTION

Figure 1:
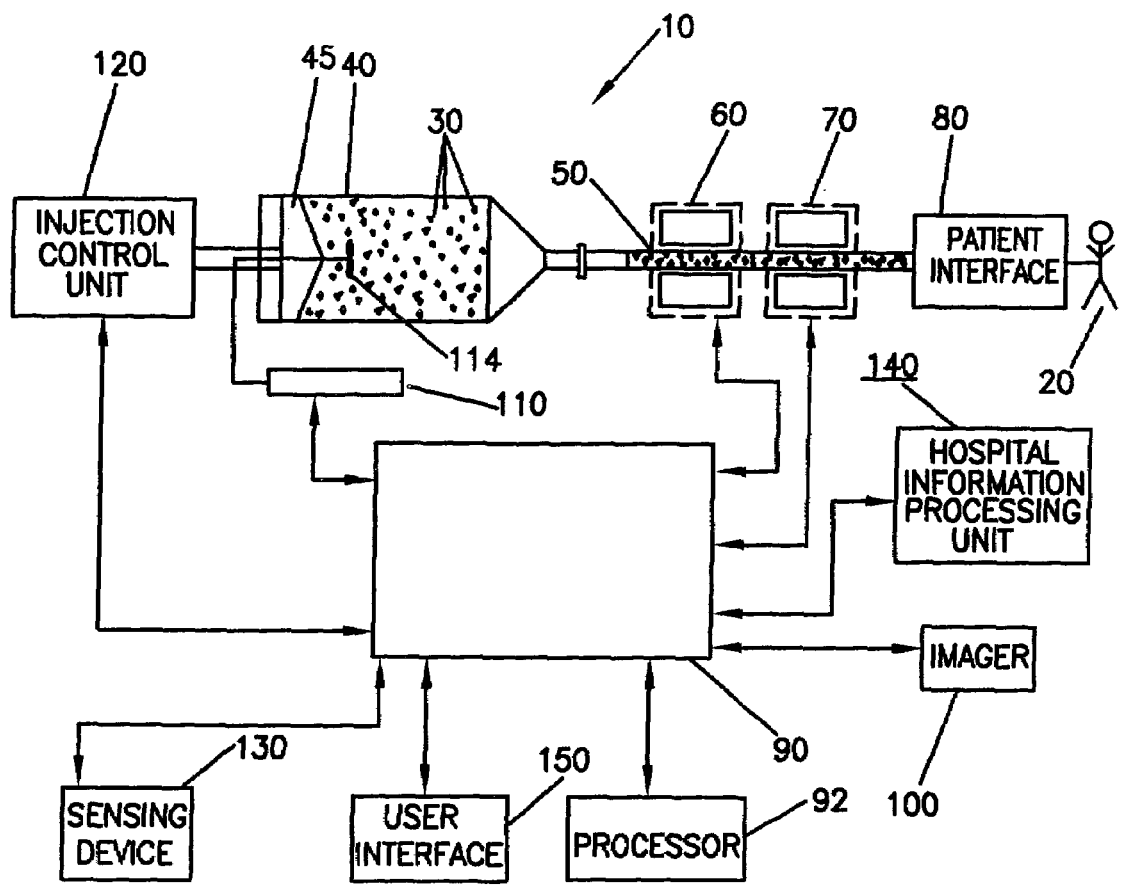
FIG. 1 illustrates an embodiment of an injection and imaging system of the present invention using ultrasonic energy to display an image of an internal region of the patient.

The present invention will be discussed, in part, with reference to a model injection and imaging system 10 illustrated in FIG. 1, in which ultrasonic energy is applied to a patient 20 to display an image of an internal region of patient 20. However, it should be understood that the present invention is also applicable to other imaging modalities, including x-ray, computed tomography, magnetic resonance imaging, nuclear imaging, and other modalities in which energy is released within or transmitted through a portion of the human body, animal, or other object to be indicated or imaged.

Ultrasound imaging creates images of the inside of the human body by broadcasting ultrasonic energy into the body and analyzing the reflected ultrasound energy. Differences in reflected energy appear as differences in gray scale or color on the output images. As with other medical imaging procedures, contrast-enhancing fluids (often referred to as contrast media) can be injected into the body to increase the difference in the reflected energy and thereby increase the gray scale or color contrast displayed in the image (that is, the image contrast) viewed by the operator.

For ultrasonic imaging, the most common contrast media contain many small bubbles (sometimes referred to as microbubbles). The difference in density of bubbles when compared to water, and thus their difference in sound transmission, makes small gas bubbles excellent means for scattering ultrasound energy. Small solid particles can also serve to scatter ultrasonic energy. Such particles are typically on the order of 1 to 10 microns (that is, $10^{-6}$ to $10^{-5}$ meters) in diameter. These small particles can pass safely through the vascular bed, and in some cases, traverse the pulmonary circulation. Contrast agents are also used for non-vascular applications such as assessment of tubal patency in gynecological applications.

Contrast media suitable for use in ultrasound are supplied in a number of forms. Some of these contrast media are powders to which liquid is added just before use. The powder particles cause gas bubbles to coalesce around them. The powder must be mixed with a liquid, and the mixture must be agitated with just the right amount of vigor to get the optimum creation of bubbles. Another type of contrast medium is supplied in a liquid form that requires hypobaric or pressure activation. A third type of contrast medium is a liquid that is agitated vigorously. There are no solid particles to act as nuclei, but the liquid is a mixture of several liquid components that make relatively stable small bubbles. A fourth type of contrast medium uses "hard" spheres filled with a gas. These contrast media are typically supplied as a powder that is mixed with a liquid. The goal is to suspend the spheres in the liquid without breaking them. Even though such spheres have a shell that is hard compared to a liquid, they are very small and relatively fragile. It is also possible for the solid particles themselves to act to scatter ultrasonic energy, but the acoustical properties of the solid spheres are not as different from water as those of a gas. Entities such as microbubbles, microspheres and solid particles suitable to enhance ultrasonic imaging contrast are referred to herein as contrast enhancement agents. For X-ray based imaging, atoms, molecules or solid particles generally absorb X-rays at a higher rate than blood and gas or gas-filled structures generally absorb X-rays at a lower rate than blood.

Contrast enhancement agents also enhance other modes of ultrasonic imaging. For example, when the microbubbles, microspheres or particles are carried along in the blood stream, the reflected energy is Doppler shifted. This Doppler shift allows an estimation of the speed of blood flow. Bubbles can also be excited so that they radiate ultrasonic energy at an harmonic of the incident ultrasonic energy. This harmonic imaging is only possible with the use of contrast medium.

After mixing/preparation as described above, the contrast medium is drawn into a syringe or other container for injection into the patient. Typically, the fluid is injected into a peripheral vein in the arm of the patient, although it may be injected into other body cavities for specific imaging procedures, for instance the intestinal tract or the female reproductive tract. When injected into the bloodstream, the blood dilutes and carries the contrast medium throughout the body, including to the area of the body being imaged (that is, the region-of-interest or ROI).

It is becoming more common for a microprocessor-controlled, powered injector to be used for injecting the contrast medium. The use of such powered injectors provides the benefit of maintaining a consistent flow over an extended time period, thereby providing a consistent amount of contrast medium in the blood stream. For ultrasound, if there are too few contrast enhancement agent particles per unit volume in the flow, however, an insufficient image contrast may result and thereby prevent an accurate diagnosis from being made. If too many contrast enhancement agent particles are present, on the other hand, excess energy is reflected, thereby resulting in blooming or saturation of the ultrasound image.

Thus, although a power injector can inject contrast medium at a constant flow rate (volume per unit time), there typically must be a generally constant number or amount of contrast enhancement agent particles per volume of fluid injected to provide a constant image contrast. If the concentration of particles changes, the image contrast will be degraded. There are many reasons why the number of contrast enhancement agent particles per volume of a certain contrast medium (and thereby the image contrast) can vary during an injection procedure. For example, density differences between the contrast enhancement agents and the fluid medium may result in separation. Moreover, the initial mixing may not have resulted in a homogeneous dispersion or suspension. Likewise, bubbles or microspheres of certain contrast media can be destroyed under conditions experienced in mixing, storage or delivery of the contrast media. Additionally, a number of conditions or parameters of the injection fluid other than the concentration of the contrast enhancing agents therein can be changed. For example, the injection flow rate, the volume of medium injected and the injection pressure can be changed in a continuous or discontinuous manner. In addition most newer ultrasound enhancement agents and most existing X-ray enhancement agents pass through the pulmonary circulation and can circulate more than once through the body, so that they build up in the patient's blood pool. The extent to which this happens differs from patient to patient. This is another reason for having feedback from the imaging system to the injector to control the injection.

Referring to FIG. 1, injection and imaging system 10 delivers a fluid medium including a suspension of microbubbles 30 suspended in a fluid carrier to patient 20. Certain components of system 10 are discussed in detail in U.S. Pat. No. 6,317,623, the disclosure of which is incorporated herein by reference.

In the embodiment of FIG. 1, a syringe or pressurizing vessel 40 drives fluid through a fluid path element 50. Fluid path element 50 may pass through a bubble or contrast enhancement agent concentration regulator 60 that can affect the enhancement properties of the agent by, for example, selectively destroying microbubbles 30. Bubbles 30 may be destroyed, for example, by insonating the fluid with ultrasound energy, generating local temperature or pressure changes in the media or by some types of mechanical agitation.

The ability to destroy microbubbles 30 in the fluid path may enable better control of the imaging procedure. Because mechanical resonance of a bubble wall is a function of bubble size, for example, it may be possible with the proper power and frequency settings to selectively decrease the concentration of bubbles of a certain size. Such selective destruction allows control of the bubble distribution. Microbubbles 30 can also be destroyed in the fluid path as part of a strategy to control contrast agent concentration. It is also possible to reduce the amount of contrast enhancing agent flowing into the patient simply by reducing the flow rate of the media.

Fluid path 50 continues through a concentration sensor 70 suitable to measure the concentration of microbubble 30 in the fluid medium. Such sensors are discussed in detail in U.S. application Ser. No. 09/267,238 referred to above.

Fluid path 50 then continues on through a patient interface 80 to an injection site on patient 80. The output of sensor 70 preferably passes to a control/communication interface 90 which may, for example, be in communicative connection with or combined with a processor unit 92 suitable to, among other things, process signals corresponding to, for example, concentration data from sensor 70 and to send control signals based upon such incoming data to other components of system 10. A control signal corresponding to the concentration data may be sent from processing unit 92 via interface 90 to any number of devices in delivery system 10 including, for example, an imaging unit such as an ultrasound scanner 100. The control signal can be used, for example, to adjust the image (for example, by increasing or decreasing the power in the signal sent into the patient, the time during which the energy is applied to the patient, the gain or other machine settings of the amplifier which receives the signal from the patient, or the speed at which the energy is scanned across the patient), to provide concentration information as part of documentation and/or to assist with diagnosis during the imaging procedure. Information can also preferably be sent from imaging unit 100 to processing unit 92 to, for example, control other devices such as, for example, an agitation/preparation mechanism 110 (including, for example, a mechanical stirrer 114), a powered injection control unit 120 and/or a concentration regulator 60.

Agitation/preparation mechanisms suitable for use in the present invention are disclosed in U.S. application Ser. No. 09/267,237, entitled AGITATION DEVICES AND DISPENSING SYSTEMS INCORPORATING SUCH AGITATION DEVICES, filed on Mar. 12, 1999, the disclosure of which is incorporated herein by reference. In that regard, several commercial agents now available require some kind of agitation or mixing for preparation. These include, but are not limited to: ALBUNEX and OPTISON available from Molecular Biosystems, Inc. of San Diego, Calif.; and LEVO-VIST available from Schering AG of Berlin, Germany.

The data communication and control devices and systems of the present invention can be used during initial preparation of the medium, during an injection procedure to effect a desired result, or after an injection to review performance and status. In that regard, certain contrast media, such as LEVO-VIST, are known to precipitate or separate over time in some of the higher concentrations (for example, 400 mg/ml). Concentration measurement can be used to detect such separation and restart or increase agitation to help reduce precipitation effects.

Concentration sensor 70 can be located anywhere on the fluid delivery path from syringe or pressurizing vessel 40 to patient interface 80. If concentration sensor 70 is located near the patient injection site at the end of fluid path 50, one can better account for microbubble degradation effects from shear rate, temperature and other delivery effects. Since sensor 70 preferably does not require direct contact with the contrast enhancement agent, a coupling piece can be made as a disposable part of a tubing set for convenience in attaching sensor 70 and or concentration regulator 60 and to maintain sterility with patient interface 80. The sensing region is preferably a known volume or area of the contrast media surface located on fluid path 50.

Other sensors or sensing equipment can be in communicative connection with interface 90. For example, a sensor or sensors (not shown) can be part of system 10 to provide direct measurements of the concentration of the fluid medium and/or the contrast enhancement agents within the patient's body. Another example is bar code readers which input information about the contrast media including but not limited to volume, concentration, manufacture date, manufacturer. Moreover, interface 90 can be in unidirectional or bi-directional communicative connection with a sensing and/or measuring device 130 that provides data on one or more physiological conditions of the patient. For example, device 130 can be a heart rate or blood pressure monitor.

Previous injector systems have contained an electrocardiograph (ECG) that is used to set start of injection trigger points synchronized with various portions of the cardiac cycle. In the present invention, other equipment such as heart rate or blood pressure monitors may be used to provide patient physiological data to control the injection or imaging process, especially during an injection. For example, during ultrasound cardiac stress echo imaging, vasodilator and vasoconstrictor drugs are administered to increase and decrease cardiac output load. Connected sensors for monitoring heart rate and blood pressure may be used to initiate, terminate or adjust the injection process when these parameters reach certain levels. The output from these sensors can also be used to adjust other aspects of the imaging process, such as scanner settings. Unlike prior systems, the present invention allows isolation, digital communication, bi-directional or two-way communication and/or communication with an imaging system.

In addition, it may be useful to control the delivery of some therapeutic or diagnostic agents during contrast imaging based on display or signal information from the imager as a result of the imaging procedure. For example, during ultrasound cardiac stress echo procedures, a drug, Dobutamine, which is a cardiotonic or cardiovascular stressor agent, is often used to increase cardiac stress so that cardiac parameters can be measured and quantified. (Dobutamine is a synthetic derivative of dopamine, characterized by prominent inotropic but weak chronotropic and arrhythmogenic properties.) An injection system may be used to control the delivery of the stressor drug during an enhanced procedure based on visual information from the imager, such as peak flow rate in a vessel from a Doppler image, the intensity of a perfused tissue region, vessel geometry measurements, or heart chamber geometry measurements during various portions of the cardiac cycle. The delivery of such a drug can also be controlled by the signal at the imager before it is generated into a display, for example, using acoustic intensitometry. This concept can be extended to other imaging modalities and to the administration of other therapeutic or diagnostic drugs or substances.

Interface 90 can also be in communicative connection with an information storage and processing unit 140 of a hospital or other care-giving organization to, for example, receive information regarding a patient to assist in control of injector controller 120 or to transmit information regarding an imaging procedure from any other device of imaging system 10 for storage and/or processing by hospital processing unit 140.

Interface 90 can also be in communicative connection with an operator interface 150 so that the operator(s) of imaging system 10 may receive information about the patient and the components of imaging system. Data, such as control parameters or algorithms, can also preferably be sent from user interface 150 to interface 90. It may be preferable to physically partition the operator interface so that some simple injection related information such as volume remaining is available near the syringe. It is preferable that all injection and scanning information be available so that the operator can quickly access relevant information during the imaging procedure. Currently, ultrasonic imagers use a display that combines the image and informative text around the image. Two different displays may be used for cost reasons or for ease of use. Information that may be displayed for operator consideration includes but is not limited to: time since the fluid was initially prepared, information such as brand or initial concentration read from contrast media packaging, initial injection parameters for a single or multilevel injection, and the status of the injector controller (for instance, disarmed, armed, injecting).

Operator interface 150 also preferably incorporates operator input devices including but not limited to keys, a track ball, a mouse, a joystick, a voice recognition system, and/or a touch panel as known in the art. These input devices allow the operator to make initial settings or to input information about the patient or the imaging procedure which the processor 92, the controller 120, or the imager 100 can use to prepare for or conduct the imaging procedure. The operator interface also enables the user to ready the injector for injection (arm the injector) or to disarm. It can also allow the operator to confirm that the proper procedure has been followed in eliminating gross air from the fluid path elements. The operator interface allows the operator to determine information used from or sent to other components such as but not limited to optional use of patient information such as patient physiologic parameters through external device interface 130 or output of selected information to the hospital processor 140.

Figure 2:
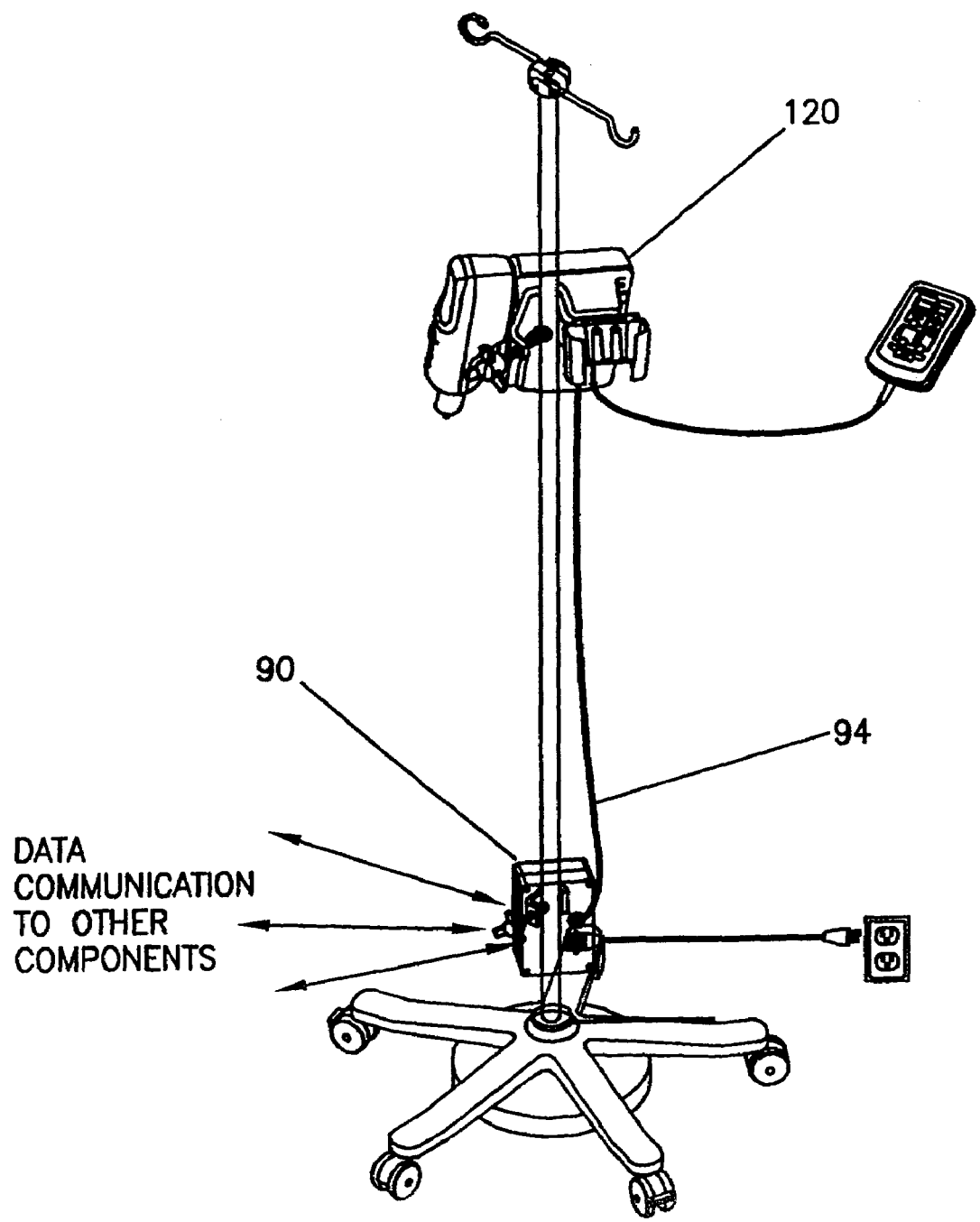
FIG. 2 illustrates an embodiment of a data communication unit of the present invention.

An embodiment of interface 90 will be discussed in the context of communication with injector control unit 120. FIG. 2, for example, illustrates an embodiment of interface 90 in communicative connection with injector control unit 120 via cabling 94. Interface 90 can preferably be connected to other devices of system 10 via any wired or wireless media for carrying the information (for example, RS-232, parallel, RS-485, LAN, etc.) using any unidirectional, paired unidirectional, or bi-directional networking or communication protocol (for example, TCP/IP, IPX/SPX, etc.) as preferably selected by an operator. Refer to Table 3 for a summary of some of the possible communication connections and protocols.

Data communication and control can be effected with use of interface 90 in part, for example, through definition of various operational states of the components of system 10. For example, a ready/armed state can be defined as the state of injector controller 120 prior to performing an injection. This state may be set upon completion of specific diagnostic functions and indicates that injector controller 120 is ready and awaiting a signal to begin an injection. An idle/disarmed state can define an idle state of injector controller 120 during which programming operations are performed. Preferably, the idle/disarmed state is the power-up default state and the state that injector controller 120 returns to after performing any injection sequence. There can be an armed multi-inject state, which allows a series of injections before returning to the idle state. Injector controller 120 is preferably always in the idle/disarmed state when connecting to or disconnecting from patient 20. A hold state of injector controller 120 is preferably entered after the operator or another system component has temporarily suspended the injection. Injector controller 120 may, for example, remain in this state for a period of time before disarming while awaiting a signal to resume the injection. An injecting state defines the state of injector controller 120 while performing an injection. This state is entered typically only from a ready/armed state.

A set of injection conditions or parameters is preferably entered into the system (for example, by an operator via operator interface 150) to define certain criteria of how an injection is to be performed. These conditions or parameters can include, for example, volume, flow rate, number of phases, fluid source or type (where A and B are two types of fluid), and whether there is a scan delay or injection delay associated with the programmed injection (that is, delivery of fluid according to a programmed injection profile).

Operational and state parameters are preferably provided between components of system 10 via interface 90 (for example, between injector controller 120 and imaging unit 100) at an update rate sufficient to allow effective real-time control of the imaging procedure (for example, to allow imaging unit 100 to produce a clear image of the injection process). For peripheral venous injections control does not need to be instantaneous because there is a variable delay from the time the fluid is injected into the patient to the time it reaches the imaging site, as well as a delay from when the fluid passes the concentration sensor 70 and the time it flows into the patient. A second function of the interface 90 is to allow control parameters to be passed between components of imaging system 10.

Typical operating parameters include, for example, programmed infusion rate, programmed bolus bate, programmed bolus volume, flow rate, total injected volume, volume remaining, bolus ready, infusion ready, bolus running, infusion running, low volume, infusion pending, bolus complete, flow profile rise/fall rates, injection aborted/canceled, error codes as well as internal diagnostic information and injector machine state. Typical control parameters may include, for example: hold injection, start injection, start scan, stop injection, stop scan, gated operations (Start/Stop) in relation to some patient parameter such as breathing or ECG, reset injector, programming commands, preparation commands, loading commands, or any other injector functions that could be activated normally by the user or by other means.

The following is an example of a data communication protocol for use with interface 90. Imaging unit 100 may, for example, include an ultrasonic scanner that operates in conjunction with an injection system (including injector controller 120 and pressurizing syringe 40) to inject a contrast agent to enhance a targeted area of concern or region of interest of patient 20. Injector controller 120 and imaging unit 100 may be interconnected via interface 90 (for example, including an RS-232 serial interface) using standard control lines Request to Send (RTS) and Clear to Send (CTS) to manage the data flow. A simple protocol may be defined wherein injector controller 120 provides all of its operating parameters via interface 90 periodically, for example every 500 milliseconds, as long as the CTS line from imaging unit 100 is set (injector controller 120 signals its readiness to imaging unit 100 by setting RTS). After receipt of a message imaging unit 100 may simply acknowledge data packets received from injector controller 120. Imaging unit 100 can also send control commands or in a separate message as necessary to control the injection/imaging process. Injector controller 120 may simply acknowledge command packets received from imaging unit 100 and may perform the requested action if it is safe to do so.

In one sequence of events, an operator sets up injector controller 120 by following all required procedures to the point where injector controller 120 is in an 'Armed' or 'Ready' state. At this point the operator can concentrate fully on operation of imaging unit 100. When ready, the operator can use a command from the imaging unit 100 to injector controller 120 (via interface 90) to begin a programmed injection. During the programmed injection and scan, the injector controller 120 is preferably providing a rapid update of its process and status. At any time, the operator preferably can abort the injection (from either the injector or imaging system or take over active control, for example, adjust the flow rate.

Interface 90 thus facilitates an integrated control feature between devices of injection and imaging system 10, permitting enhancement of diagnostic information. System 10 gives an operator the provisions to manage many or all of the components of system 10 (and, thereby, all facets of the injection and imaging procedure) from the most convenient place. Indeed, a single operator can easily perform a contrast-enhanced scan using the procedural ease afforded by the integrated approach of system 10. Any number of quantification algorithms that expand the diagnostic capability of the system can utilize the information provided over interface 90 to maximize the quality and diagnostic utility of the images.

For example, there are numerous applications for an ultrasound injector with a bi-directional data and control communications interface 90, especially in the areas of closed loop control of injector controller 120 based on an acquired signal or image. Such applications may be divided broadly into two classes, diagnostic and therapeutic.

As a diagnostic application, a communication interface 90 between injector controller 120 and scanner 100 can be used to detect lesions and tissue characteristics through differences in tissue vascular concentration or perfusion. The technique is useful as a method for tumor detection and identification. Closed loop control can, for example, be used to provide relatively constant enhancement of tissue within a region of interest to help identify tumors in those areas.

Video density, video intensity, acoustic intensity or acoustic Doppler intensity information (that is, raw acoustical data) from scanner 100 can be used to control the injection profile (for example, as a way to control injected enhancement agent concentration) to provide the desired time response and level of enhancement. An algorithm in processor unit 92 or control unit 120 can accommodate for delays between a change in an injection parameter such as flow rate and the appearance of the change at the imaging site. Because tumors are often hyper-vascular or hypo-vascular relative to surrounding normal tissue, tumors can be identified by differences in enhancement level or enhancement level changes over time. A similar technique can be used to observe and quantify tissue perfusion during contrast enhanced myocardial echocardiography or other perfusion studies.

Closed loop control can be used to control the concentration of the enhancement agent in a region of tissue. The level of enhancement required, the level of enhancement or the time response of enhancement increase or decay can be used to observe tissue perfusion, since the enhancement agent will be present in the small vessels that perfuse the region of interest. This technique can also be combined with the use of vasoconstrictor/vasodilator drugs, physical stress, or other means to induce cardiovascular stress to make changes in perfusion more pronounced or detectable.

Another diagnostic application for interface 90 is to control parameters such as concentration, flow rate or time or timing of injection based on data of a physiologic parameter, such as heart rate, provided by external device 130. An example of a procedure is closed loop drug delivery of cardiac stress agents while imaging. In this technique, a stressor agent is injected and controlled based on heart rate. Once a target heart rate is achieved it may be useful to synchronize and control the level of injected enhancement agent, or to provide bolus injection control for diagnostic purposes. In that regard, information from imaging unit 100 can be used to control the delivery of the enhancement agent. Interface 90 can also be used to terminate an injection if a certain level of enhancement has not been reached within a certain time period, preventing waste of the imaging agent and saving procedure time. Or it can simply warn the operator that conditions are outside some optimal window and let the operator take appropriate actions. This technique can be generalized to injection communication and control based on information from other external equipment or patient physiological parameters.

Information from the concentration sensor 70 can be used to affect the injection parameters, or it can simply be communicated via interface 90 to the operator interface 150 so that the operator has access to the concentration information during the imaging procedure. The operator is the one who takes action to adjust the injection, stop the procedure or take other appropriate action. This has a potential advantage in achieving quicker regulatory approval for the manufacture and sale of the device. This allows the operator to make the decision versus the system taking action automatically, which may require more validation effort. Also data from concentration sensor 70 could be transmitted to the imager 100 directly or after processing in the processor 92 so that parameters of the imaging unit mentioned elsewhere can be adjusted to achieve a satisfactory diagnostic image in spite of changes in concentration of the contrast-enhancing agent.

There are also many therapeutic and other applications of imaging system 10. For example, enhancement agents may be used as a means for site-specific imaging and for activated drug or gene therapy delivery. For example, ImaRx of Tucson, Ariz. has an agent under development, MRX-408, based on their previous agent DMP-115 (DEFINITY), a multilipid encapsulated perfluoropropane and air echo enhancing agent that incorporates site specific binding for the detection of thrombus. Some ultrasound and x-ray imaging agents are being developed that release drugs or are "activated" when insonated or bombarded with x-ray energy. Image video intensity, acoustic intensity, acoustic Doppler intensity or other image information can be used with these agents to track and control the concentration of an agent within a region over time. Coupled with injector controller 120 and interface 90 for injection control, the delivered agent concentration or total agent dose can be controlled for maximum therapeutic effect and to prevent overdose.

For example, a certain drug delivery imaging agent can be injected under control of imaging system 10 so that the observed enhancement is stabilized at a target level for a certain period of time. During this time, the drug of the agent can be activated within the region of interest using, for example, ultrasound or x-ray energy. Once the time period of sufficient enhancement expires, the injection can be terminated by control from imaging unit 100. Information on the injection delivery history (e.g., the flow rate profile) and total dose (e.g., total volume delivered) can be sent to the imaging unit 100 or hospital processing unit 140 for record keeping and documentation purposes. Other methods, such as using the time integral of image pixel intensity, can be used to measure and control the total delivered dose of the agent. With microbubble-based delivery of active substances in ultrasound, information from the imaging unit 100 can also be used to make sure that all of the agent within a certain region has been completely activated before ending the injection, maximizing the delivered dose within the region of interest. Other agents may become available in the future that are activated by electromagnetic (especially optical), magnetic, or nuclear radiation. All such activation energy sources are suitable for use in the present invention.

Another application of real-time data and control interface 90 is for control of pulsed flow for therapeutic applications. In pulsed flow thrombolysis, for example, high flow rate but short duration bolus injections are used to both mechanically disrupt or ablate and chemically dissolve thrombi in vessels. Image information regarding the progress of clot dissolution can be used to communicate changes to the injection system flow rate, agent concentration, pulse duration and other fluid delivery parameters. While not shown in the figure, a duplicate injector with duplicates to syringe 40 and control unit 120 could be injecting the therapeutic agent into the patient and cooperating through interface 90 with simultaneous or alternating injections of therapeutic agent, flushing agent (such as saline) and imaging agent. In some applications it can be advantageous to control the injection of three (3) or more fluids by using multiple injection mechanisms in communications with each other through interface 90.

In certain therapeutic injections, it is desirable to synchronize the delivery of short boli of therapeutic fluid with that portion of the cardiac cycle that ensures turbulent mixing with blood. Without turbulent mixing, these toxic fluids can be entrained in streamlines of laminar flow, which carry the fluid beyond the area of intended application. In this case, the fluid is typically introduced by a peripheral arterial access. A precise volume of fluid must be injected by breaking it up into small volume packets timed to the cardiac cycle. A communications link to injector controller 120 can be used to control the timing of fluid delivery in this application.

Figure 3:
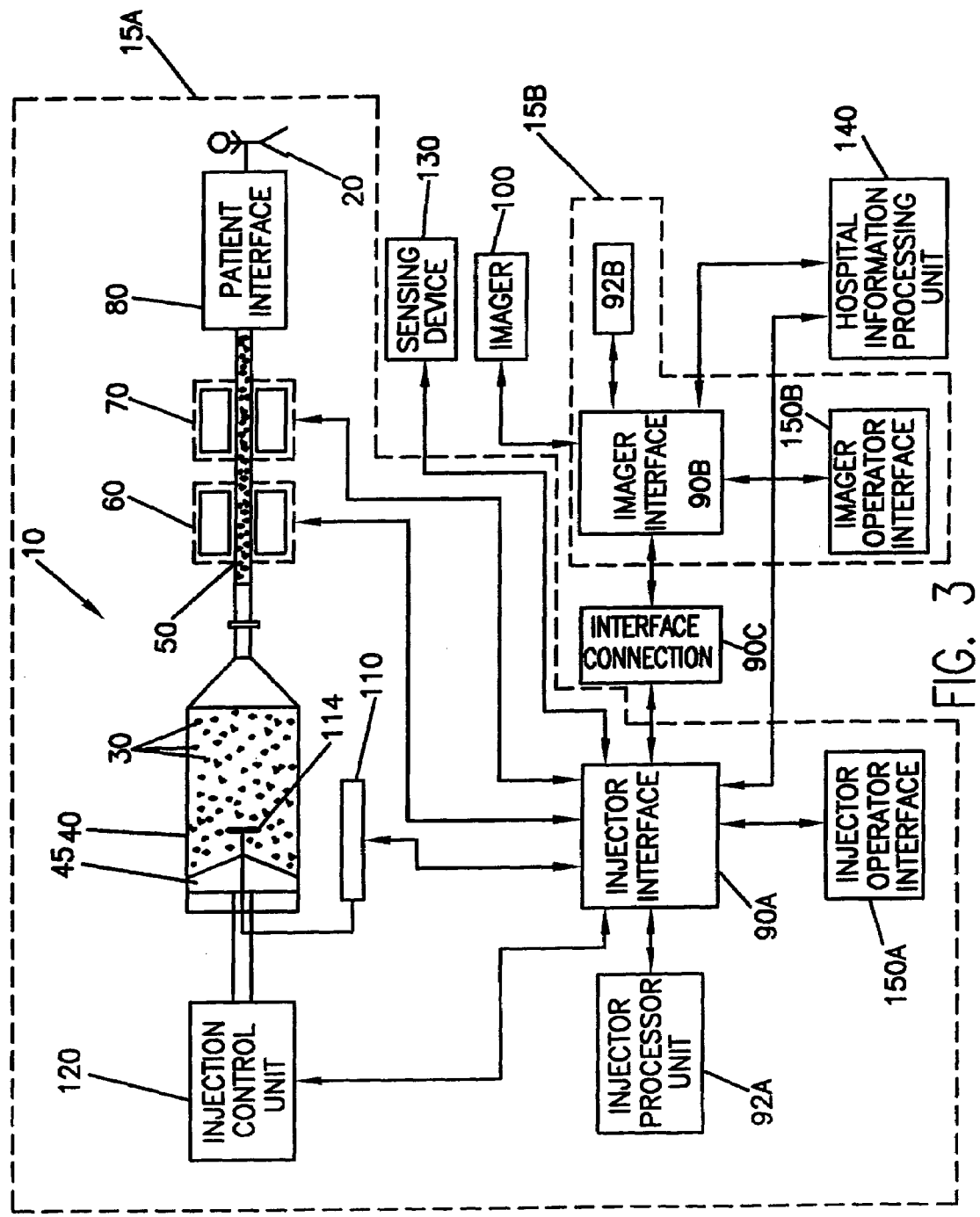
FIG. 3 illustrates another embodiment of an injection and imaging system of the present invention.

FIG. 3 illustrates an example of a block diagram that partitions the functions described above between separate injection subsystems and imaging subsystems. This embodiment may, for example, accommodate a situation in which the various subsystems are separately manufactured by the same or different manufacturers and/or a situation in which the subsystems require separate regulatory approvals.

In FIG. 3, the unpartitioned components retain the same numbers as in FIG. 1. For those that are partitioned between the two subsystems, those partitioned into injector subsystem 15a of the system generally include a suffix "a" and those partitioned into imager subsystem 15b generally include a suffix "b." Component 90c is the interface connection between the two subsystems.

Injector subsystem 15a includes generally those elements for the control of the fluid flow. Injector subsystem 15a includes, for example, concentration sensor 70 and external device 130. Injector processor unit 92a takes and receives information from an injector operator interface 150a and the other components through injector interface 90a.

Imager subsystem 15b includes generally elements for the control of the imaging energy and the creation of an image or measurement as discussed above. Imager subsystem 15b includes, for example, a processor unit 92b that takes and receives information from an imager operator interface 150b and the other components through imager interface 90b.

It is possible for the subsystem components to be partitioned in other ways. For instance, concentration sensor 70 might be part of the imager subsystem 15b. The same applies to external device 130. FIG. 3 shows both subsystems having separate communications to the hospital information system 140. It may be that only one of the subsystems communicates with the hospital interface 140. Other partitioning is possible as well.

All communications between the two subsystems preferably take place through subsystem interface 90c. A benefit of this partitioning is the isolation of the need for the most stringent error control and verification to the operation of subsystem interface 90c. Communications within each subsystem can be more easily tested as a self-contained unit.

Present imaging systems use a simple relay closure as an interface between subsystems so that one subsystem can tell the other to start a preprogrammed function. By having a subsystem interface 90c transmit information, many of the above listed benefits are possible.

In addition to timing information communicated via relay closures by prior systems, the data transmission enabled by the present invention includes, for example, information sent between devices regarding operating parameters, operator input, device status information, and control sequencing. In addition, data transferred from one device to another device can be used to enable active control of the receiving device from that data. For example, during the injecting state, data transmission from an ultrasound scanner can be sent to an injector to enable active control of the injection flow rate based on the data received.

The discussion below provides a list of example capabilities possible with interface 90c between the subsystems of the present invention. Many of these have also been discussed above. Injector subsystem 15a can send information about its state or its programs to imaging subsystem 15b such as, but not restricted to:

Contrast enhancing fluid type or volume, read by bar code or operator input
Contrast enhancing fluid concentration
Time since mixing of the contrast enhancing fluid
Time since last injection
Time since start of current injection
Time of last servicing
Injector system unique identification number or code
Injector hardware or software configuration (version number)
Status of agent agitation, for instance, mixing or ready
Current Selected Infuse Rate
Current Selected Bolus Rate
Current Selected Bolus Volume
Current injection Phase
Actual Flow Rate
Actual Volume Delivered Total Injected Volume
Volume Remaining
Bolus Ready
Bolus Low Volume
Bolus Running
Bolus Complete
Infuse Ready
Infuse Running
Infuse Pending
Injection Stopped or Canceled
Injector Error Detected and Type Information such as set forth above can be used by imager subsystem 15b to adjust its operation to optimize the image acquisition process as described above. It can also be displayed on the imager subsystem operator interface so that it is convenient for the operator to assess the injector subsystem's functioning. It may be that imager subsystem 15b cannot automatically adjust its operation based upon the transmitted information, but that the operator has to make an adjustment. The information could be displayed at the imager to allow the operator to view the information before making adjustments. This may be for regulatory approval or to simplify subsystem design verification.

Information can also be transmitted from imager subsystem 15b to injector subsystem 15a. This information may be used to adjust the injector subsystem operation as mentioned above, or it may simply be displayed so the operator at the injector user interface 150a can be informed about key imager subsystem information. A basic benefit is the ability to start and stop the injection from imager operator interface 150b. A much more sophisticated capability is to be able to program all injector functions from the imager subsystem operator interface 150b as if the operator were at injector subsystem operator interface 150a. An example of a middle ground is if injector subsystem 15a communicates possible preprogramming sequences to imager subsystem 15b, and the operator at imager operator interface 150b chooses among the sequences.

Another benefit of data communication between subsystems is the ability for imager subsystem 15b or the operator at imager subsystem operator interface 150b to determine that an image or measurement was not sufficient and command the injector to repeat the injections or to perform a different injection. A planned example of this is what is often termed a test injection. After an injection is made and a series of images or measurements are acquired, scanner/imager processor unit 92b or injector processor unit 92a can determine from the information gathered the injection parameters, including timing, that are most likely to create the desired enhancement in the final image or measurement.

Given the criticality of the information being transmitted between the two subsystems, it is desirable that there be significant safeguards to prevent error or problems. In a preferred embodiment, the electrical signals of the two subsystems are not electrically connected to each other, which can be accomplished in many ways. Optical isolators, isolation transformers and capacitance based isolators commonly used components for providing electrical isolation. Other means of isolation are by the use of transmitted or broadcast electromagnetic or ultrasonic energy for the transmission means.

It is also preferable that each subsystem be able to operate even if interface 90c is not operating. This result can be accomplished within the programming of each subsystem processor unit. If the operator tries to use a function that requires communications between subsystems, and communications are not available or in an unknown state, the operator is preferably either informed of that condition, or an attempt to communicate is made and the operator is informed of the results of that attempt.

It is also preferable to structure data transmission so that errors are avoided or tolerated. The discussion below provides an example procedure to provide error detection and tolerance. The example discusses information transmission from injector subsystem 15a to imager subsystem 15b with acknowledgement of proper receipt by imager subsystem 15b being sent to injector subsystem 15a, but the same methodology can be readily applied with the respective roles reversed to transmit information in the other direction. The use of two separate transmission channels can be used as discussed below. A single transmission channel can also be used.

EXAMPLE

In one embodiment, injector subsystem 15a periodically transmits status information through subsystem interface 90c to imager subsystem 15b, which preferably only has to acknowledge the successful (or unsuccessful) data reception. In this embodiment, imager subsystem 15b does not request data from injector subsystem 15a or send data other than acknowledgements to injector subsystem 15a. A message based flow control mechanism is preferably used to regulate the data flow from injector subsystem 15a.

In this embodiment, only two different messages are preferably sent from injector subsystem 15a to imager subsystem 15b. The injector subsystem interface status message preferably contains the interface software version number and indicates if injector status information is available, and the injector status message preferably contains, for example, injection parameter values and volume information. The injector subsystem interface status message is preferably transmitted when connection is established or resumed, which is determined by the status of the handshake lines. It is preferably sent approximately every 500 milliseconds (not including retries) as long as injector status information is not yet or no longer available. If injector status information is available and the injector subsystem interface status message has been acknowledged, the injector status message is preferably transmitted approximately every 500 milliseconds (not including retries).

The following discussion provides a detailed description of the communication protocol and the format of the two messages discussed above.

Data Exchange Mode

Communication may, for example, be serial, asynchronous and full duplex at 19200 Baud with flow control using RTS/CTS. Each data frame sent between the two subsystems preferably comprises ten bits: one start bit (logic 0), eight data bits (LSB first, no parity), and one stop bit (logic 1). The start and stop bits preferably have the same width as data bits. The electrical interface is preferably designed to be compatible with the EIA RS-232.V28 standard.

Message Format

Messages sent from injector subsystem 15a to imager subsystem 15b preferably have the format set forth in Table 1:

TABLE 1

| STX | Sequence Number | Message Length | Message Data | CRC | ETX |
|---|---|---|---|---|---|
| 1 byte | 1 (2) byte | 1 (2) byte | up to 48 (96) byte | 1 (2) byte | 1 byte |

Numbers in parenthesis in Table 1 represent the actual size during transmission after data folding has been performed. Data folding is discussed below.

STX

The STX (start of text) transmit) transmit) transmit) character indicates the beginning of a message. The one byte hexadecimal code for STX is, for example, 0x02.

Sequence Number

Figure 4:
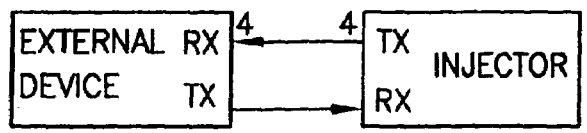
FIG. 4 illustrates an example of internal transmit and receive sequence numbering.
Figure 4:
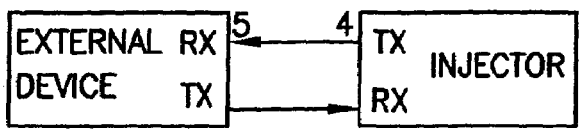
Figure 4:
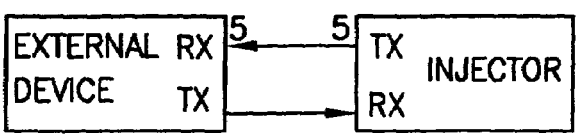

A one-byte sequence number is preferably used to enable the receiving system to detect a retransmitted message. The sequence number is necessary for the case that a message is successfully transmitted and received but the receiver's acknowledge becomes corrupted. The transmitting system preferably retransmits the message after a response time-out has occurred. As the receiver already received the message successfully the first time, it can identify the message as a duplicate by checking the sequence number against the sequence number of the last received message. The receiver preferably acknowledges and then discards the duplicate message. The receiver, therefore, preferably maintains a receive sequence number which is set to the sequence number of a received message after it has been validated. The transmitter also preferably maintains a transmit sequence number which represents the sequence number of the last message for which a positive acknowledge was received. An example of internal transmit and receive sequence numbering for a message transmission and the receiver's response is illustrated in FIG. 4.

Message Length

The one byte Message Length field specifies the size of the following Message Data field in bytes. The Message Length value range is, for example, 1 to 48.

Message Data

This portion of the message is the data portion of the message. If a message contains data items comprising multiple bytes, the byte order is preferably little endian (least significant byte first). Examples of supported messages and associated message format are discussed in further detail below.

CRC

An eight-bit CRC is preferably used to secure the data to be transmitted. It enables the receiving system to detect message data corruption. The CRC covers the Sequence Number, Message Length, and Message Data fields before folding. An example of a polynomial used to calculate the CRC is: $x^8+x^4+x^2+x+1$.

ETX

The ETX (end of text) character indicates the end of a message. The one byte hexadecimal code for ETX is, for example, 0x03.

Message Acknowledge

As mentioned above, the receiving system preferably acknowledges each received message by sending a single control character. The transmitting system preferably does not transmit a new message until the last transmitted message has been acknowledged or a response time-out has occurred. An acknowledge can be positive (ACK), indicating successful message reception and CRC validation, or negative (NAK), indicating an invalid CRC or a receive time-out. The injector preferably retransmits a message until it receives a positive acknowledge. If a status message has to be retransmitted and updated status information is available, a new message with the updated status is preferably sent instead. The one byte hexadecimal code for an ACK is, for example, 0x06. A NAK is represented as hexadecimal 0x15.

Data Folding

To avoid data escaping, all bytes between the STX and ETX control characters are preferably 'folded' to guarantee that their values fall within the printable ASCII character range (0x20 to 0xE7) and do not overlap with control characters. This result is achieved by splitting each byte into two nibbles and adding a fixed offset to each nibble. The offset to be used is preferably 0x30. Folding the data between the STX and ETX, therefore, doubles the size of a message. An example message and the folded data to be transmitted are given below in Table 2:

TABLE 2

| | Original Message | Folded Message |
| --- | --- | --- |
| STX | 0x02 | 0x02 |
| Sequence Number | 0x10 | 0x30, 0x31 |
| Message Length | 0x02 | 0x32, 0x30 |
| Message Data | 0x45, 0x67 | 0x35, 0x34, 0x37, 0x36 |
| CRC | 0xB6 | 0x36, 0x3B |
| ETX | 0x03 | 0x03 |

Handshaking

Figure 5:
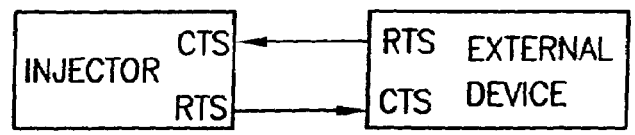
FIG. 5 illustrates an embodiment of a connection between an injection system and external device, showing physical layer control signals.

Two hardware signals (CTS and RTS) may be used to implement a message based flow control as described above. The signals may also be used to detect connection between injector subsystem 15a and imager subsystem 15b. FIG. 5 illustrates the signals and how they are connected.

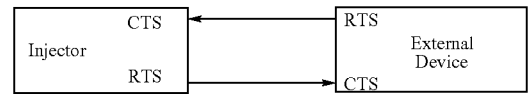

Connection Establishment

The injector preferably activates RTS once it is ready to transmit data to imager subsystem 15b. The RTS signal preferably stays active as long as injector subsystem 15a is powered up and operating normally. Initial connection is preferably established when injector subsystem 15a has activated its RTS output and detects its CTS input as active for the first time. Connection is preferably resumed when injector subsystem 15a detects its CTS input as active after it had been deactivated. Imager subsystem 15b can activate its RTS output (the injector's CTS input) at any time; it is not required to wait for injector subsystem 15a to activate its RTS output first.

Flow Control

Figure 6:
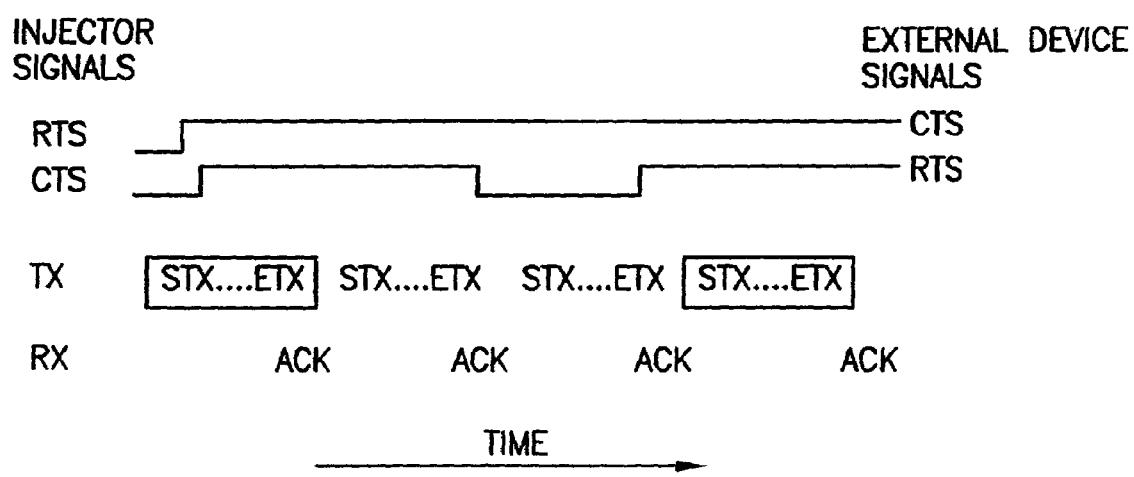
FIG. 6 illustrates an embodiment of the communications protocol between an injector system and external device, showing message flow control.

Injector subsystem 15a preferably transmits the injector subsystem interface status message when connection is initially detected or resumed. Once injector status information is available and the injector subsystem interface status message has been acknowledged (ACK), injector subsystem 15a preferably transmits the injector status message about every 500 milliseconds, not including retransmits. As long as imager subsystem 15b does not deactivate its RTS signal, injector subsystem 15a preferably continues its periodic transmission. If imager subsystem 15b deactivates its RTS output, injector subsystem 15a preferably finishes the current message transmission. It then waits for imager subsystem 15b to activate its RTS signal again. When the imager subsystem's RTS output is active again, injector subsystem 15a preferably restarts transmission with an injector subsystem interface status message. FIG. 6 illustrates a flow control example: (INJECTOR SUBSYSTEM interface status messages are indicated by a solid border).

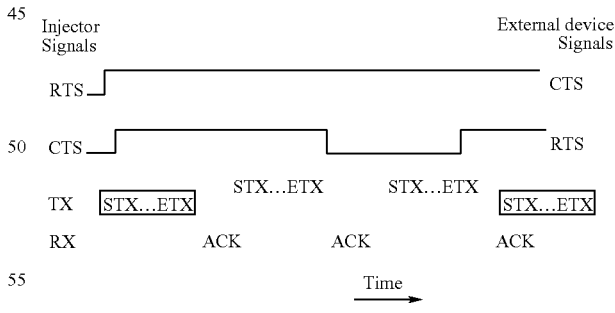

Time-Outs

The requirement that each successfully received message be acknowledged by the receiver, has the side effect that the transmitter can potentially wait forever for an acknowledge (ACK/NAK). Another possible error condition is that the transmitter aborts the transmission before the ETX character is sent. A set of time-outs are preferably used to allow the transmitting and receiving systems to recover from these situations.

A time-out duration may, for example, be based on the following calculations: At a baud rate of 19200 it takes about 52 microseconds to transfer one data bit. One data byte (a 10 bit frame) can, therefore, be transmitted in about 520 microseconds. Assuming no delay between bytes, transmission of a maximum length message (104 bytes, folded) takes approximately 54.1 milliseconds. The required one-byte response from the receiver adds another 520 microseconds, not taking any validation and processing of the received message into account.

Transmit Time-out:

A message transmission time-out may be used to account for situations in which the transmission of a message never completes or takes too long because of an internal transmitter problem. If a transmission time-out is not incorporated, the injector could possibly wait forever for the completion of a message transmission, which would block the transmission of all subsequent messages. As previously discussed, a maximum length message can be transmitted in a minimum of 54.1 milliseconds. Allowing some delay between bytes because of processing overhead, the transmit time-out may, for example, be set to 60 milliseconds. The transmit time-out period begins with the STX character being transmitted.

Receive Time-out:

A message receive time-out may be used to account for situations in which the reception of a message never completes (e.g. ETX missing) or takes too long. If a receive time-out is not incorporated into the design the imager subsystem could possibly wait forever for the reception of a message to complete which would block the reception of all subsequent messages. Since the timing associated with the reception of a message is dictated by the transmitter, the same value as for the transmit time-out (60 milliseconds) may be used. The receive time-out period begins when the STX character is received.

Response Time-out:

A message response time-out may be used to account for situations in which imager subsystem 15b does not acknowledge or takes too long to acknowledge a received message. Even though imager subsystem 15b does not send any messages in this embodiment and an acknowledge could therefore be expected after a few milliseconds, the response time-out is also preferably set to 60 milliseconds. The response time-out period preferably begins when the ETX character is transmitted.

The section below provides a brief summary of the handling of a number of error situations by the present communication interface system.

Error Handling

Injector Subsystem

Transmission Time-out: The time to transmit an entire message exceeded the transmission time-out period. This error indicates an internal problem of the injector transmitter. The injector will deactivate its RTS signal, indicating that no further messages will be sent to the imager subsystem. RTS will remain deactivated until power is cycled off/on and the injector is ready to transmit data again.

Response Time-out: The imager subsystem did not respond to a message within the response time-out period. The injector will retransmit the last message unless updated status information is available which would be transmitted instead of the last message.

NAK Received: The imager subsystem did not properly receive a message (CRC mismatch, receive time-out). The injector will retransmit the last message unless updated status information is available which would be transmitted instead of the last message.

Imager Subsystem

Receive Time-out: The time that it took to receive a message exceeded the receive time-out period. The imager subsystem will send a NAK to request a retransmit of the message.

STX Character Missing: Other data are received when waiting for an STX character. The imager subsystem will discard all characters until an STX is received. If the injector was trying to send a message, a response time-out will occur and the message will be sent again.

CRC Mismatch: The CRC calculated from the received data did not match the received CRC value. The imager subsystem will send a NAK to the injector after the receive time-out period has expired.

Duplicate Message Number: The received message number was equal to the last message number received. The imager subsystem will send an acknowledge and disregard the retransmitted message.

Dropped Data Bytes: During reception of a message one or more data bytes were lost. This error will most likely result in a CRC mismatch. The imager subsystem will send a NAK to the injector after the receive time-out period has expired.

Message Data Format

The Message Data portion of a message as discussed above may have the format set forth in Table 3 below.

TABLE 3

| ID | ID specific data |
|---|---|
| (1 byte) | (up to 47 bytes) |

Supported IDs

Figure 7:
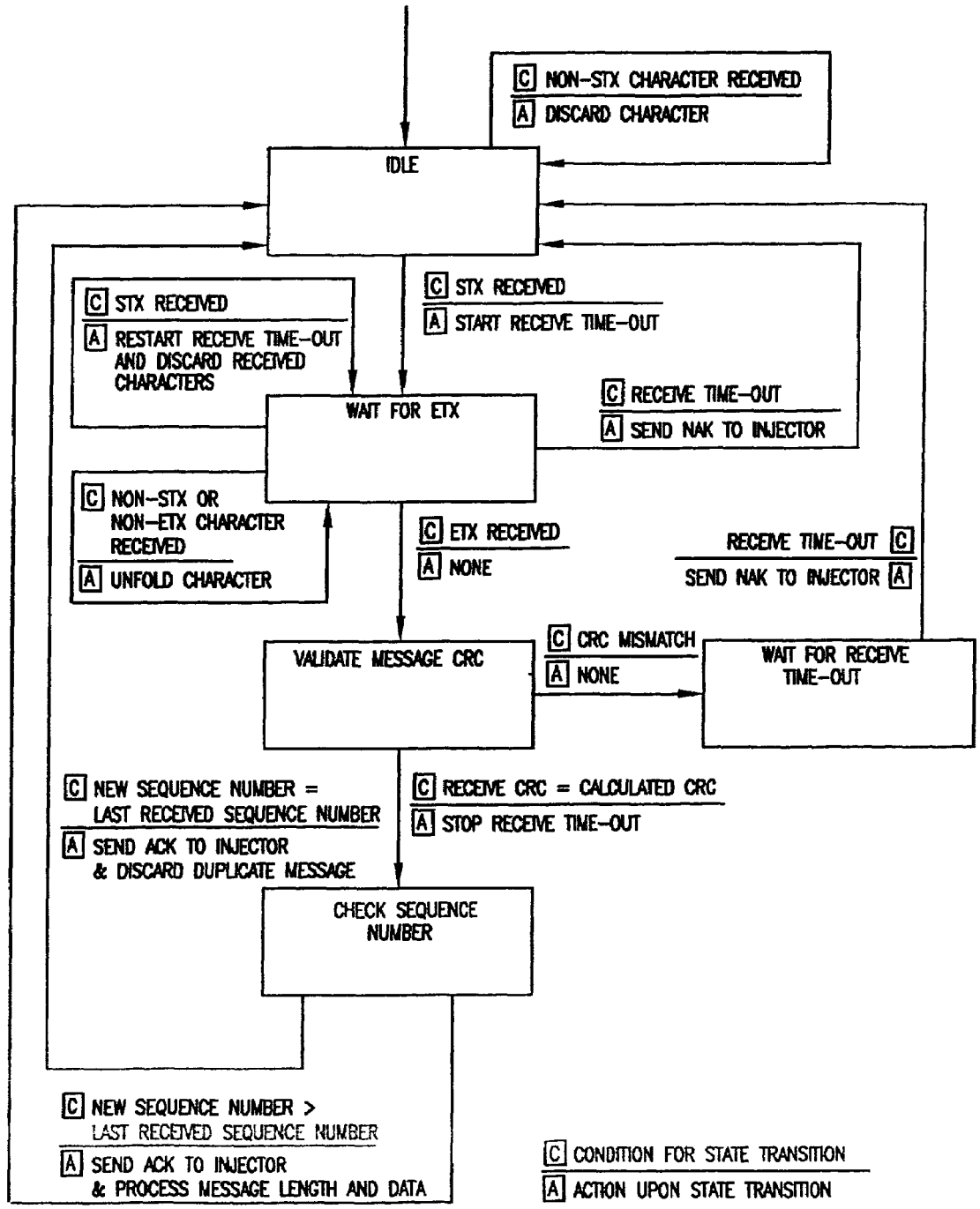
FIG. 7 illustrates an example of a state transition diagram of the receive processing to be performed by an external device communicating with an injector subsystem of the present invention.

Examples of supported messages and associated data for external device interface status and injector status are provided in Tables 4 and 5, respectively. Binary data of word size are transmitted in little endian byte order. FIG. 7 illustrates a state transition diagram of the receive processing to be performed by an external device (for example, imager subsystem 15b) communicating with injector subsystem 15a.

TABLE 4

| Field | Encoding | Data Type | Value Range | Description |
|---|---|---|---|---|
| ID | Binary | Byte | 0xF5 | |
| Data | | 7 | | |
| Injector Status Data Available | Binary | Bit 7 | 0 or 1 | The bit is 1 when injector status information is available for transmission. |
| Reserved | N/A | Bit 6-0 | N/A | |
| SW Version | ASCII | Char [4] | '1.0' to '99.9' | |
| Reserved | N/A | Byte [2] | N/A | |

TABLE 5

| Field | Encoding | Data Type | Value Range | Description |
|---|---|---|---|---|
| ID | Binary | Byte | 0xFA | |
| Data | | | | |
| Programmed Infusion Rate | Binary | Word | 0 to 290 | The value is given in tenths ml/min. The actual range therefore is 0.0 to 29 ml/min Resolution: 0.5 ml/min between 0.0 and 10, 1 ml/min between 10 and 29 |
| Programmed Bolus Rate | Binary | Word | 0 to 30 | The value is given in tenths ml/s. The actual range therefore is 0.0 to 3.0 ml/s. Resolution: 1.0 ml/s |
| Programmed Bolus Volume | Binary | Word | 0 to 30 | The value is given in ml. Resolution: 1 ml |
| Flow Rate | Binary | Word | 0 to 1800 | The value represents a non-cumulative running average while an injection is in progress. It will be 0 before and after an injection. The value is given in tenths ml/min. The actual range therefore is 0.0 to 180 ml/min. During a bolus, the external device should convert the received flow rate value to units of ml/s. |
| Total Injected Volume | Binary | Word | 0 to 9990 | The value is given in tenths ml. The actual range therefore is 0.0 to 999 ml. Resolution: 0.5 ml between 0.0 and 100, 1 ml between 100 and 999 |
| Volume Remaining | Binary | Word | 0 to 300 | The value is given in tenths ml. The actual range therefore is 0.0 to 30.0 ml. Resolution: 0.5 ml |
| Bolus Ready | Binary | Bit 7 | 0 or 1 | The bit is 1 when the injector is ready for an injection and both bolus parameters are > 0. The bit is 0 at any other time, including during a bolus. |
| Infusion Ready | Binary | Bit 6 | 0 or 1 | The bit is 1 when the injector is ready for an injection and the infusion rate is > 0. The bit is 0 at any other time, including during an infusion |
| Bolus Running | Binary | Bit 5 | 0 or 1 | The bit is 1 while the injector is performing a bolus. The bit is 0 at any other time. |
| Infusion Running | Binary | Bit 4 | 0 or 1 | The bit is 1 while the injector is performing an infusion. The bit is 0 at any other time. |
| Low Volume | Binary | Bit 3 | 0 or 1 | The bit is 1 if the programmed bolus volume is less than the volume remaining. If this condition becomes true during a bolus, Low Volume will not be indicated until the bolus ends to avoid operator confusion. The bit is 0 at any other time. |
| Infusion Pending | Binary | Bit 2 | 0 or 1 | The bit is 1 if an infusion was interrupted by or requested during a bolus and will resume after the bolus ends. The bit is 0 at any other time. |
| Bolus Complete | Binary | Bit 1 | 0 or 1 | The bit is 1 when a bolus completes (programmed volume is delivered). It is 0 at any other time. Note that the bit is only set for one message. |

TABLE 5-continued

| Field | Encoding | Data Type | Value Range | Description |
|---|---|---|---|---|
| Injection aborted/canceled | Binary | Bit 0 | 0 or 1 | The external device is responsible for latching this information if desired. The bit is 1 when an injection is aborted or canceled e.g. due to an invalid key press or running out of volume. The bit is 0 at any other time. Note that the bit is only for one status message. The external device is responsible for latching this information if desired. |
| Error Code | ASCII | Char [3] | ' ' or 'A 1' to 'Z99' | Three spaces indicate no error. The currently supported error codes are listed below: P1: Perform check for air P2: No volume remaining P3: Pressure stall P4: Syringe attached P5: Syringe removed S1: Disarm due to key press C: Critical Error 'P' codes require an operator acknowledge, 'S' codes time out after five seconds 'C' requires injector power to be cycled. |

Layering

A summary of a preferred embodiment of the layering involved in the present example is presented in Table 6.

TABLE 6

| OSI Layer | Key Layer Functions/Services | Preferred Methods | Other Representative Methods |
|---|---|---|---|
| Layer 1. - Physical Layer | Physical connections, physical service data units (n-bit transmission), physical connection end points, sequencing, data circuit identification, fault condition notification, quality of service parameters (error rates, service availability, transmission rates, delays) | RS-232.V28 | thinnet, thicknet, unshielded twisted pair (UTP), RS-232-C, FDDI, ISN, wireless RF, wireless infrared |
| Layer 2. - Data Link Layer | Data link connection, data link service data units, error notification, flow control, quality of service parameters | Ack>/<Nak> message control, start of message <Stx> and end of message <Etx> formatting, message numbering scheme, transmit and receive retries (optional), duplicate message number detection and handling, CRC-16 error detection and correction operations | Ethernet, token ring, HDLC |
| Layer 3. - Network Layer | Data packet routing | Not used | Internet Protocol (IP, SLIP, CSLIP, PPP), Internet Control Message Protocol (ICMP), Internet Group Management Protocol (IGMP) |
| Layer 4. - Transport Layer | Error recovery and flow control, message multiplexing | Not used | Transmission Control Protocol (TCP), User Diagram Protocol (UDP) |

TABLE 6-continued

| OSI Layer | Key Layer Functions/Services | Preferred Methods | Other Representative Methods |
|---|---|---|---|
| Layer 5. - Session Layer | Control structure for managing communications, session connection, session management, session termination, interaction management | Outgoing data is not sent (session not initiated) unless external device enables communication through CTS | Remote Procedure Call (RPC) |
| Layer 6. - Presentation Layer | Common operations on the structure of the data being exchanged, syntax conversion, syntax negotiation, encryption, compression | Message coding and decoding, data folding | External Data Representation (XDR) |
| Layer 7. - Application Layer | Communication management between applications, synchronization of applications, availability determination, file transfer access, job transfer | Fixed protocol, no negotiation. Injector and imager share timing and control information to perform the imaging procedure. | SMTP, SNMP, ftp, telnet, DNS, INS, NFS, arp, rlogin, talk, ntp, traceroute |

All medical products are regulated by government bodies in some way. This approval process includes validation and verification that the equipment performs properly under all conditions. As discussed above, it is possible that injector subsystem 15a will be designed and manufactured by one company and that imager subsystem 15b will be designed and manufactured by another. In fact, there may be multiple manufacturers for each. Subsystem interface 90c may be manufactured by any of the above, or even be manufactured by a totally different company. As also discussed above, the equipment functions may be coordinated by a human operator to perform the imaging needed to determine the diagnosis. It is very difficult to test a piece of equipment under all possible conditions when it has to communicate and cooperate with another piece of equipment. Even if two pieces of equipment are manufactured by the same company, they are often designed by separate teams and there are thus still coordination and testing difficulties. In addition, there may be a problem with changes or improvements to one piece of equipment being compatible with older or newer versions of the other equipment. It is, therefore, desirable that standard interfaces, such as the EIA RS-232.V28 standard be used in the present invention. To sufficiently isolate injector and imager subsystems 15A and 15b, it is preferred that subsystem interface 90c be powered separately and be isolated from both of the subsystems. This has a regulatory and validation benefit.

Although the present invention has been described in detail in connection with the above embodiments and/or examples, it is to be understood that such detail is solely for that purpose. For example, many of the functions separately called out and described can be performed by identical pieces of hardware. These and other variations can be made by those skilled in the art without departing from the spirit of the invention except as it may be limited by the following claims.

What is claimed is:

1. A method of controlling an imaging procedure, the method comprising the steps of:
    (a) providing an integrated injection and imaging system featuring an injector subsystem and an imaging subsystem, with the imaging subsystem for applying energy to a patient and producing an image or a measurement of an internal region of the patient from a signal resulting from the energy applied to the patient, and with the injector subsystem having first and second pressurizing units for pressurizing a contrast medium and a diluent, respectively, for injection into the patient in connection with the imaging procedure; and
    (b) providing a data interface interconnecting the injector and imaging subsystems for enabling exchange of digital information therebetween, the information comprising at least timing data, such that the digital information transmitted between the subsystems is usable thereby for enabling closed loop control of one of the subsystems by the other of the subsystems through which the contrast medium and the diluent injected into the patient is adjustable so as to achieve a desired level of enhancement therewith within the internal region of the patient of which the images are acquired during the imaging procedure;
    wherein the closed loop control of one of the subsystems by the other of the subsystems is based upon at least one of (i) selected portions of the digital information from the imaging subsystem, (ii) selected portions of the digital information from the injector subsystem, and (iii) a physiological condition of the patient obtained from a sensor thereof.

2. The method of claim 1 wherein at least some of the digital information transmitted from the imaging subsystem is usable by the injector subsystem to modify one or more parameters of the injection.

3. The method of claim 2 wherein the injection parameters include at least one of concentration, flow rate, timing, volume, pressure, temperature, time since preparation, brand, type, number of phases, sequencing of mediums, therapeutic progress, and patient recirculation related data.

4. The method of claim 2 wherein the closed loop control enables the injection parameters to be adjusted based on one or more physiological parameters of the patient.

5. The method of claim 2 wherein the injection parameters are stored for use for subsequent or other injection procedures.

6. The method of claim 1 wherein at least some of the digital information transmitted from the injector subsystem is usable by the imaging subsystem to modify one or more parameters of the imaging system.

7. The method of claim 6 wherein the imaging parameters include at least one of power in the energy sent into the patient, time during which the energy is applied to the patient, gain of an amplifier which receives the signal from the patient, or speed at which the energy is scanned across the patient.

8. The method of claim 6 wherein the closed loop control enables the imaging parameters to be adjusted based on one or more physiological parameters of the patient.

9. The method of claim 6 wherein at least some of the digital information transmitted from the imaging subsystem is usable by the injector subsystem to modify one or more parameters of the imaging subsystem.

10. The method of claim 1 wherein the digital information includes control parameters, the control parameters comprising at least one of hold injection, start injection, start scan, stop injection, stop scan, reset injector subsystem, and gating control operation based on feedback from a physiological parameter of the patient.

11. The method of claim 1 wherein the data interface includes:
    (a) an injector interface unit associated with the injector subsystem;
    (b) an imager interface unit associated with the imaging subsystem; and
    (c) an intermediate interface unit linking the injector and imager interface units and thereby enabling the exchange of the information between the injector and imaging subsystems.

12. The method of claim 11 wherein the injector interface unit is for enabling the exchange of a desired portion of the information with at least one of:
    (a) a processor unit of the injector subsystem;
    (b) an operator interface device associated with the injector subsystem, the operator interface device for use in at least one of entering initial settings, entering at least some of the digital information, entering programming for at least one of the injector and imaging subsystems, and functioning as a display for at least one of the injector and imaging subsystems;
    (c) a hospital information system from which additional patient information is receivable and usable thereby as part of the digital information;
    (d) a physiological sensor from which a condition of the patient is receivable and usable thereby as part of the digital information; and
    (e) a fluid sensor from which a condition of the contrast medium is receivable and usable thereby as part of the digital information.

13. The method of claim 11 wherein the imager interface unit is for enabling the exchange of a desired portion of the information with at least one of:
    (a) a processor unit of the imaging subsystem;
    (b) an operator interface device associated with the imaging subsystem, the operator interface device for use in at least one of entering initial settings, entering at least some of the digital information, entering programming for at least one of the injector and imaging subsystems, and functioning as a display for at least one of the injector and imaging subsystems;
    (c) a hospital information system from which additional patient information is receivable and usable thereby as part of the digital information;
    (d) a physiological sensor from which a condition of the patient is receivable and usable thereby as part of the digital information; and
    (e) a fluid sensor from which a condition of the contrast medium is receivable and usable thereby as part of the digital information.

14. The method of claim 1 wherein one or more desired portions of the digital information are storable in at least one of the injector subsystem, the imaging subsystem, and an external information system, and retrievable therefrom.

15. The method of claim 1 wherein the data interface is connectable to at least one additional injector subsystem to enable exchange of the digital information therebetween to effect closed loop control of at least one of the injector subsystems by the imaging subsystem.

16. A method of controlling an imaging procedure to enable diagnosis and therapeutic treatment of diseased tissue in a patient, the method comprising the steps of:
    (a) providing an injection and imaging system featuring an injector subsystem and an imaging subsystem, with the imaging subsystem capable of applying energy to and producing an image of an internal region of the patient from a signal resulting from the energy applied to the patient, and with the injector subsystem capable of injecting at least one of a contrast medium and a therapeutic agent into the patient in connection with the imaging procedure;
    (b) providing a data interface interconnecting the injector and imaging subsystems for enabling exchange of digital information therebetween, the digital information comprising at least timing data; such that the digital information transmitted between the subsystems is usable thereby for enabling closed loop control of one of the subsystems by the other of the subsystems through which concentration of the contrast medium injected into the patient is adjustable in connection with the imaging procedure during which the images are acquired;
    (c) exchanging a desired collection of the digital information between the subsystems and thereby coordinate through the data interface the imaging procedure performed by the imaging subsystem with the injection of the contrast medium into the patient by the injector subsystem to produce a contrast-enhanced image at a desired enhancement level of the internal region including the diseased tissue thereat; and
    (d) administering the therapeutic agent via the injector subsystem for the purpose of targeting the diseased tissue for treatment therewith.

17. The method of claim 16 wherein the enhancement of the contrast-enhanced image of the internal region of the patient is stabilized at a target level for a desired period of time to enable the therapeutic agent to be activated thereat.

18. The method of claim 17 wherein the therapeutic agent is activated by at least one of ultrasound, x-ray, electromagnetic, magnetic, and nuclear radiation energy.

19. The method of claim 16 further including the step of connecting a sensor to one of the data interface, the injector subsystem and the imaging subsystem through which a physiological condition of the patient is made available to the system as part of the digital information and usable thereby.

20. The method of claim 19 further including the step of adjusting parameters of at least one of the injection and the imaging procedures based at least in part on feedback obtained from the sensor on the physiological condition of the patient.

21. The method of claim 16 further including the step of connecting a sensor to one of the data interface and the injector subsystem through which a condition of the contrast medium is made available to the system as part of the digital information and usable thereby.

22. The method of claim 21 further including the step of adjusting parameters of at least one of the injection and the imaging procedures based at least in part on feedback obtained from the sensor on the condition of the contrast medium.

23. The method of claim 16 further including the step of transferring to a hospital information system a desired subset of the information pertaining to at least one of the injection of the contrast medium, the administration of the therapeutic agent, and the imaging procedure.

24. The method of claim 16 further including the step of connecting a hospital information system to the data interface through which patient information is exchangeable therebetween and usable thereby as part of the digital information.

25. The method of claim 16 wherein at least some of the digital information transmitted from the imaging subsystem is usable by the injector subsystem to modify one or more parameters of the injection.

26. The method of claim 25 wherein the injection parameters for at least one of the contrast medium and the therapeutic agent include at least one of concentration, flow rate, timing, volume, pressure, temperature, time since preparation, brand, type, number of phases, sequencing of mediums, therapeutic progress, and patient recirculation related data.

27. The method of claim 16 wherein at least some of the digital information transmitted from the injector subsystem is usable by the imaging subsystem to modify one or more parameters of the imaging system.

28. The method of claim 27 wherein the imaging parameters include at least one of power in the energy sent into the patient, time during which the energy is applied to the patient, gain of an amplifier which receives the signal from the patient, or speed at which the energy is scanned across the patient.

29. The method of claim 16 wherein at least some of the digital information transmitted from the imaging subsystem is usable by the injector subsystem to modify one or more parameters of the imaging subsystem.

30. A method of controlling an imaging procedure to enable stress testing of a cardiovascular system of a patient, the method comprising the steps of:
(a) providing an injection and imaging system featuring an injector subsystem and an imaging subsystem, with the imaging subsystem capable of applying energy to and producing an image of an internal region of the patient from a signal resulting from the energy applied to the patient, and with the injector subsystem capable of injecting at least one of a contrast medium and a cardiovascular stressor agent into the patient in connection with the imaging procedure;
(b) providing a data interface interconnecting the injector and imaging subsystems for enabling exchange of digital information therebetween, the information comprising at least timing data; such that the digital information transmitted between the subsystems is usable thereby for enabling closed loop control of one of the subsystems by the other of the subsystems through which concentration of the contrast medium injected into the patient is adjustable in connection with the imaging procedure during which the images are acquired;
(c) connecting a sensor to one of the data interface, the imaging subsystem and the injector subsystem through which a cardiac condition of the patient is made available to the system as part of the digital information and usable thereby;
(d) exchanging a desired collection of the information between the subsystems and thereby coordinate through the data interface the imaging procedure performed by the imaging subsystem with the injection of the contrast medium into the patient by the injector subsystem to produce a contrast-enhanced image at a desired enhancement level of the internal region; and
(e) administering the cardiovascular stressor agent via the injector subsystem for the purpose of stressing the cardiovascular system.

31. The method of claim 30 further including the step of controlling the administration of the cardiovascular stressor agent based on feedback obtained from the sensor on the cardiac condition of the patient.

32. The method of claim 30 further including the step of adjusting parameters of at least one of the injection and the imaging procedures based on feedback obtained from the sensor on the cardiac condition of the patient.

33. The method of claim 30 further including the step of connecting a contrast sensor to one of the data interface and the injector subsystem through which a condition of the contrast medium is made available to the system as part of the digital information and usable thereby.

34. The method of claim 33 further including the step of adjusting parameters of at least one of the injection and the imaging procedures based at least in part on feedback obtained from the contrast sensor on the condition of the contrast medium.

35. The method of claim 30 wherein the sensor is at least one of a heart rate monitor and a blood pressure monitor.

36. The method of claim 30 wherein the internal region of the patient includes the heart.

37. The method of claim 30 further including the step of adjusting parameters of at least one of the injection and the imaging procedures to stabilize the enhancement of the contrast-enhanced image of the internal region of the patient at a target level for a desired period of time once a target heart rate has been achieved.

38. The method of claim 30 wherein at least some of the digital information transmitted from the imaging subsystem is usable by the injector subsystem to modify one or more parameters of the injection.

39. The method of claim 38 wherein the injection parameters for at least one of the contrast medium and the cardiovascular stressor agent include at least one of concentration, flow rate, timing, volume, pressure, temperature, time since preparation, brand, type, number of phases, sequencing of mediums, and patient recirculation related data.

40. The method of claim 30 wherein at least some of the digital information transmitted from the injector subsystem is usable by the imaging subsystem to modify one or more parameters of the imaging system.

41. The method of claim 40 wherein the imaging parameters include at least one of power in the energy sent into the patient, time during which the energy is applied to the patient, gain of an amplifier which receives the signal from the patient, or speed at which the energy is scanned across the patient.

42. The method of claim 30 wherein at least some of the digital information transmitted from the imaging subsystem is usable by the injector subsystem to modify one or more parameters of the imaging subsystem.

43. The method of claim 30 wherein the digital information includes control parameters, the control parameters comprising at least one of hold injection, start injection, start scan, stop injection, stop scan, reset injector subsystem, and gating control operation based on feedback from a physiological parameter of the patient.

* * * * *